United States Patent [19]

Nakamura et al.

[11] Patent Number: 5,527,359
[45] Date of Patent: Jun. 18, 1996

[54] METHOD OF MAKING POSITIVE AND NEGATIVE MODELS FOR ARTIFICIAL BREASTS

[75] Inventors: Toshiro Nakamura; Tetsuya Watanabe, both of Oda, Japan

[73] Assignee: Nakamura Brace Co., Ltd., Shimane, Japan

[21] Appl. No.: 399,882

[22] Filed: Mar. 7, 1995

Related U.S. Application Data

[62] Division of Ser. No. 19,457, Feb. 18, 1993, abandoned.

[30] Foreign Application Priority Data

Feb. 18, 1992  [JP]  Japan .................................. 4-69409
Feb. 18, 1992  [JP]  Japan .................................. 4-69410

[51] Int. Cl.⁶ ............................. A61F 2/52; B29C 33/40
[52] U.S. Cl. ..................... 623/7; 264/222; 264/DIG. 30
[58] Field of Search ............................... 623/7, 8, 11, 66; 264/222, DIG. 30

[56] References Cited

U.S. PATENT DOCUMENTS

| | | | |
|---|---|---|---|
| 4,086,666 | 5/1978 | Vaskys et al. | 623/8 |
| 4,397,701 | 8/1983 | Johnson et al. | 156/62 |
| 5,258,036 | 11/1993 | Edenbaum et al. | 623/33 |

*Primary Examiner*—Debra S. Brittingham
*Attorney, Agent, or Firm*—Darby & Darby

[57] ABSTRACT

Described is an artificial mamma and a series of molds for producing the mamma, in which the mamma comprises a bag-like member which has as a skin a thick film member made of silicon rubber and interposing therein an elastic fabric as a core enclosing air internally, the thick film member being partially larger in thickness to provide a point where an air injection needle is inserted. The mold for producing the mamma can be constructed from ordinary materials and without the need for specialized technicians.

10 Claims, 4 Drawing Sheets

FIG. 1
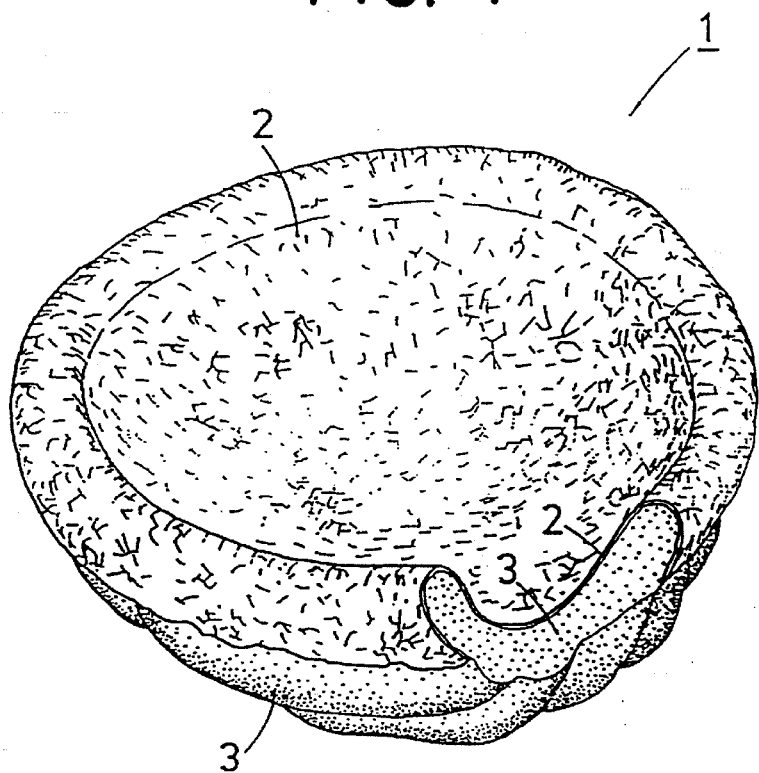
FIG. 11A
FIG. 11B
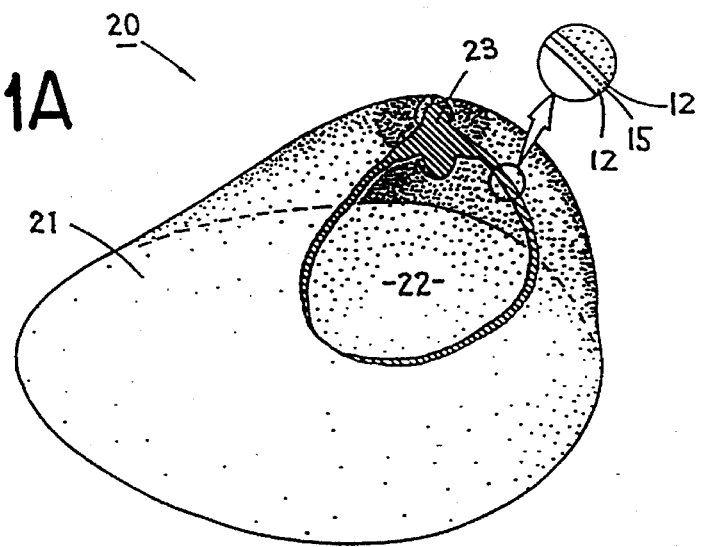

METHOD OF MAKING POSITIVE AND NEGATIVE MODELS FOR ARTIFICIAL BREASTS

This is a division, of application Ser. No. 08/019,457, filed Feb. 18, 1993, now abandoned.

BACKGROUND OF THE INVENTION

1. Field of the Invention

The invention relates to an artificial mamma to be used by applying it onto female breasts without embedding therein, and a structure of a negative model (mold) for use in producing the artificial mamma.

2. Prior Art

The artificial mammae which are employed to remedy disproportionate right and left mammae due to ateliosis or to provide prostheses for mammae affected by operations are classified generally into those that are placed in undergarments or the like, and those that are surgically embedded in the breasts.

The former type of artificial mammae which are not surgically embedded are especially useful for those women who have had breast related operations, such as breast cancer surgery, or other conditions where the breast surface is affected, since the artificial mammae can provide the outward appearance of a normal breast. This type of artificial mammae is free of danger and safe in use, so that they my be applied in most cases, including such cases where the artificial mammae are used as basic elements for remedying disproportionate right and left mammae due to ateliosis. This type of artificial mammae basically comprises silicon jelly or urethane foam coated with silicon rubber.

The artificial mammae are commercially available in the form of ready-made products. But, properly speaking, they should be individually produced due to inherent differences in the shape of female mammae. It is believed that the more an artificial mamma is similar to an excised mamma, the more a woman's disappointment from the mammary ablation can be reduced. This is particularly so for a woman who has one of her mammae removed or partially removed due to mammary cancer or the like, wherein ablation is carried out generally for only one of the mammae because of a low possibility of occurrence of cancer in both mammary glands.

Described herein is a means for making an artificial mamma for women who have undergone mammary ablation due to mammary cancer or other conditions and do not wish to use a ready-made artificial mamma. A mammary model (mold) is first formed based on the remaining mamma, since that mamma to which the mammary model ought to properly correspond has been already excised. Gypsum (plaster bandage is used usually) is coated around the remaining mamma and hardened to form a "negative model", followed by forming a positive model using the negative model as a master form. A mating mold is then formed-based on the positive model, in which melted silicon rubber and other materials are injected, followed by various processes to obtain the desired artificial mamma.

The model-making process using the affected woman's mamma itself as a basic model uses gypsum and thereby requires that the woman be restrained from moving away from the site until the gypsum is hardened. Hence, in addition to the fundamental problem that it is difficult to model a normal shape of the mamma due to its deformation under pressure, it is quite embarrassing for the woman to cause her mamma, deformed by earlier operations or disease, to be exposed to others even in the confined space for the process.

Also, the resulting artificial mammae produced by the above procedure impose psychological, physical and economic burdens on the users. Namely, these artificial mammae are apt to be heavier and also uncomfortable in use due to large differences in deformation under pressure between the artificial mamma and the corresponding original mamma. Additionally, in relation to the former defect, i.e., that it is apt to be heavier, most of the artificial mammae require additional use of special undergarments (such as brassieres or the like). Furthermore, no conventional artificial mammae can make adjustments for elasticity and fine adjustments corresponding to a change in the user's figure and other factors, thereby necessitating producing of new artificial mammae for each occasion.

SUMMARY OF THE INVENTION

The present invention is directed to and characterized by an artificial mamma comprising a bag-like member which has as a skin a thick film member made of silicon rubber and interposing therein an elastic fabric as a core and enclosing air internally, the thick film member being partially larger in thickness to provide a point where an air injection needle is inserted. The invention is also directed to and characterized by a negative model to be used for forming a positive model from which an artificial mamma is produced, the negative model comprising an inner surface portion made of aluminum foil and an outer surface portion made of plastic in a foaming-hardening type.

An important objective of the present invention is to obviate the need for silicon jelly and other materials, which are heavy and cause discomfort in the use of the artificial mamma. The invention achieves this result by instead using silicon rubber, which is soft and superior in adaptability to human skin, but is poor in resistance to tearing. The poor resistance to tearing is compensated for by employing an improved technique for strengthening the silicon rubber without deteriorating its stretchability. The improved technique uses an elastic fabric as a core material, with silicon rubber serving as the main body. The elastic fabric improves the strength of the silicon rubber without deteriorating its elasticity. The elastic fabric is, preferably, similar to stockings or hosiery which are thin and well stretchable.

Regarding the negative model for producing the artificial mamma, an important objective is that the model-making process producing a model directly of a real mamma be able to be carried out easily without requiring the skill or services of a technician. This feature enables any woman to obtain a desired artificial mamma without the necessity of going to a special office or clinic.

The negative model and the positive model produced, therefrom are not always final models, since right and left inverted artificial mamma may be produced from these models through the same procedures, as mentioned below.

In detail, one possible application may be to make an artificial mamma before ablation of the natural mamma. In this case, the natural mamma is covered with aluminum foil. The aluminum foil is deformed corresponding to the shape of the mamma and coated with a foam-hardening type of urethane resin liquid. The urethane resin hardens to form a negative model. A corresponding positive model based on the negative model can then be a final model for producing the artificial mamma.

In the case where any affected mamma has already been excised or a mamma for which an artificial mamma is to be provided has been already deformed, it is impossible to make a model directly from the affected mamma. In this case, a negative model made of aluminum foil is first formed based on the normal mamma that is opposite to the affected mamma, in order to obtain a corresponding positive model. This is followed by reversing the right and left sides of the positive model to obtain an inverse positive model. Alternatively, the models may be produced when not based on real mammae. In any case, the present invention does not at all limit the method for deforming aluminum foil.

BRIEF DESCRIPTION OF THE DRAWINGS

FIG. 1 is a perspective view showing an example of a model for an artificial mamma according to the present invention.

FIG. 11 is a partially cut out perspective view showing an example of an artificial mamma according to the present invention.

DETAILED DESCRIPTION OF THE INVENTION

The present invention will be further detailed with reference to examples shown in the attached drawings.

FIG. 1 is a perspective view showing an example of a negative model 1 for artificial mamma according to the present invention (referred to herein as "aluminum model 1"). As shown, the aluminum model 1 comprises an aluminum foil 2 having a concave surface extending along the shape of the mammae and a foamable polyurethane resin 3 placed outside the aluminum foil 2 (at the side of the convex surface of the aluminum foil). The aluminum foil 2 may be ordinary aluminum foil that is commonly sold for household use and the foamable polyurethane resin 3 may be "Hiprene-foam" (aerosol type, Mitsui Toatsu Chemicals, Inc.) which is used for heat insulating material, soundproof material or filler. The Hiprene-foam is a single liquid type, easy-foaming, and hardening polyurethane foam which quickly foams when applied, and expands about two times and hardens by moisture. The polyurethane foam is superior to the aluminum foil 2 in adhesion, shape-keeping property, and is also light in weight. Other plastics may also be used for this purpose.

The curved surface of the artificial mamma is generally formed by actually placing aluminum foil over a real mamma to deform the foil according to the shape of the real mamma. The aluminum model 1 in the present example was completed in this manner. A practical characteristic of the model according to the present invention is that the model can be relatively easily made at home since the aluminum foil and the foaming-hardening type plastic are commercially available and no other devices or facilities and special skill are required. Hence, the invention does not require that users to go to a special facility and expose their breasts to the technicians for the model-making process used to obtain an artificial mamma. This is especially important for women whose breast have been affected by disease or other conditions. Also, the users can discreetly obtain an artificial mammae which may be sent by mail.

FIGS. 2 through 10 show schmetically and step by step, an example of an actual procedure of making an artificial mamma by means of the aluminum model 1. The explanation and illustration will be given for the case that the model-making is carried out at the right mamma to prepare an artificial left mamma.

Figure 2:
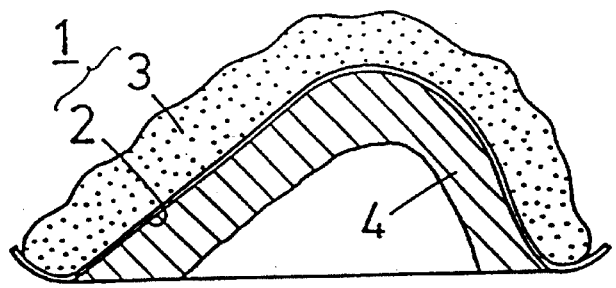
FIGS. 2 through 10 are schematic sectional views showing a course of the process for making the artificial mamma.
Figure 3:
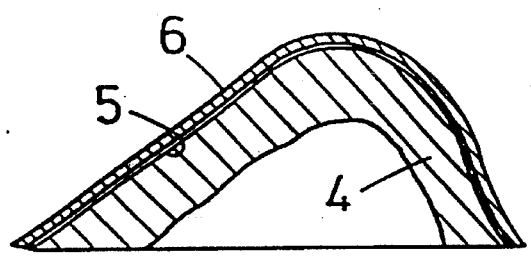

First, aluminum model 1 is used as a mold and plaster is applied to form a positive model 4 of a right mamma (called hereunder "a right positive model 4") (FIG. 2). The aluminum model 1 is removed and the right positive model 4 is coated on the surface with aluminum foil 5, which is then reinforced as a whole by a thin adhesive taping 6 which does not have substantial stretchability (FIG. 3).

Figure 4:
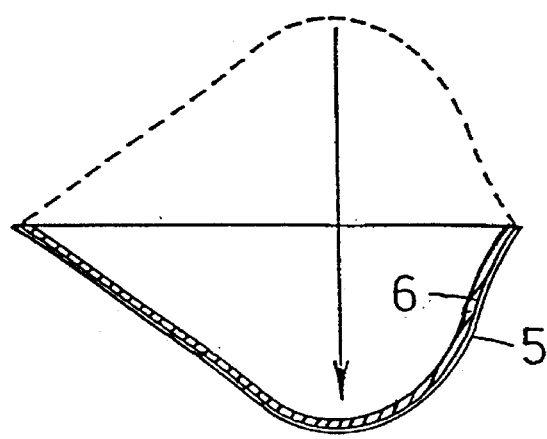

The aluminum foil 5 reinforced with the adhesive taping 6 is reversed with the concave and convex parts being inverted (FIG. 4). When the aluminum foil 5 is first reversed (for example, by pushing with the fingers from the opposite side), the foil deforms due to the pressure being applied. The continuous pushing procedure gradually transforms the foil into a symmetrical, inverted shape. When the foil has been completely inverted, it can no longer be expanded since the adhesive taping 6 cannot be extended by normal finger force. This procedure results in a symmetrical shape which is used to provide a negative model for the left mamma.

Figure 5:
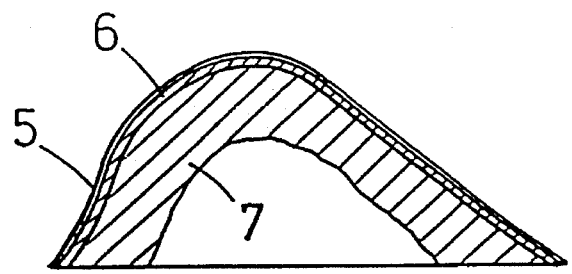
Figure 6:
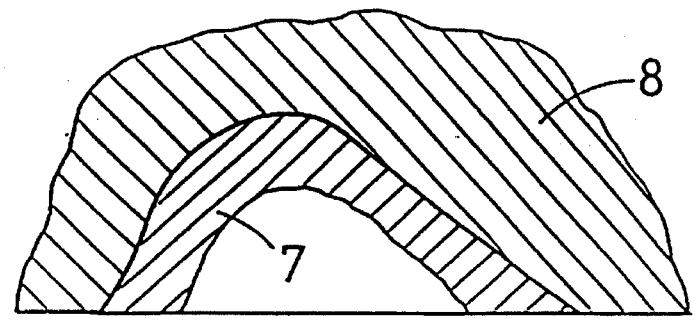

Next, the reversed aluminum foil 5 is used as the negative model and plaster is applied to form a left positive model 7 (FIG. 5). After completion of the left positive model 7, the aluminum foil 5 is removed and surface treatment is carried out on the left positive model 7. In this example, the left positive model 7 is not used as a mold for injecting silicon resin.

A left negative model 8 is prepared using the left positive model 7 as a mold (FIG. 6) to which plaster is applied. The inner surface of the resultant left negative model 8 is a very important surface for forming the surface of the artificial mamma.

Figure 7:
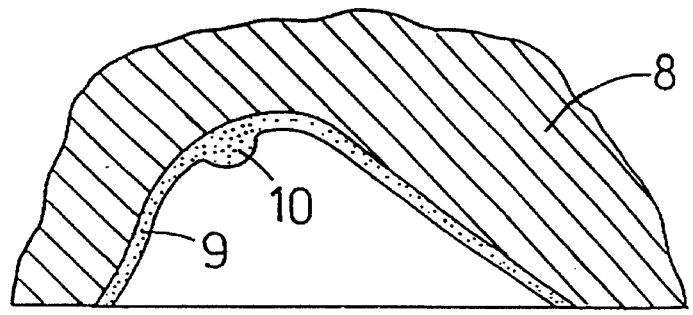

Foamable plastic or the like 9 is then formed on the inner surface of the left negative model 8 in a desired thickness corresponding to the intended artificial mamma (FIG. 7). The formed plastic or the like 9 is not uniform in thickness but is provided with a lump-like shaped larger thickness part 10 at a point corresponding to the inner side of a nipple. For easy removal of the foamable plastic 9, release agent may be previously coated on the inner surface of left negative model 8.

Figure 8:
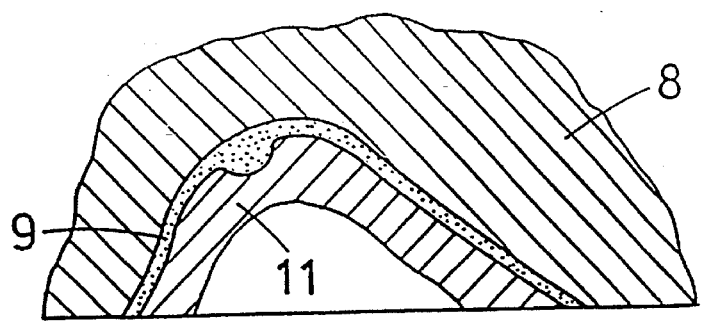
Figure 9:
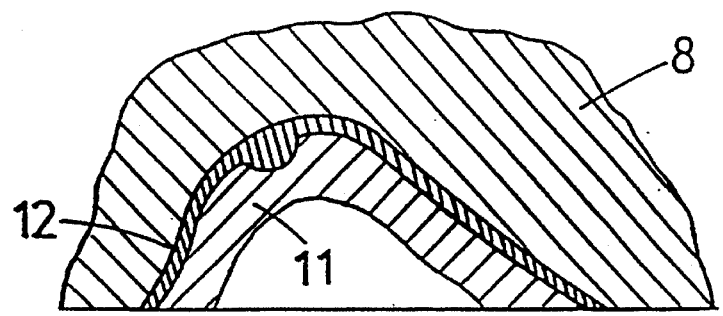

Plaster is then applied on the inner surface of the foamable plastic 9 to make a final left positive model 11 (FIG. 8). After hardening of the plaster, the foamable plastic 9 is removed. The resultant left positive model 11 and the left negative model 8 are used as a mating mold and melt of silicon rubber 12 is injected in a gap between the models 8 and 11 (FIG. 9). Since silicon rubber 12 does not provide sufficient strength (particularly, resistance to tearing), elastic fabric 15, such as stockings or hosiery, is previously inserted into the gap between the models 8 and 11 and the silicon rubber melt 12 is then injected in the gap.

Figure 10:
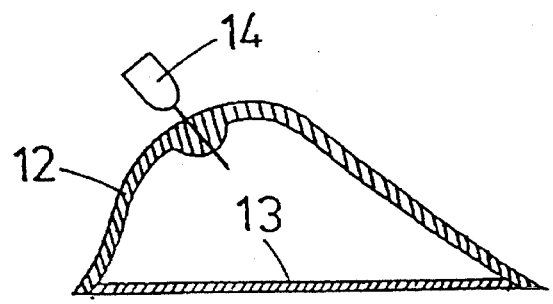

In this example, the silicon rubber melt 12 after being injected in the gap was left to stand at room temperature for about 10 hours to be fully hardened and was then removed from the mold. The time for hardening the silicon rubber may be shortened by heating the silicon rubber. The removed silicon rubber is joined with a bottom lid 13 to form a bag-like shape as a whole, and air is injected through the nipple part by use of an air injection needle 14 to complete the artificial mamma 20 (FIG. 10).

The method of making shown in FIGS. 2 through 10 employs four plaster molds. The number of plaster molds to be used may be reduced, for example, by using the left positive model 7 as one component of the mating mold. In this case, a resultant artificial mamma is larger than the actual right mamma (with which the model-making was carried out) to the extent of the thickness of the silicon rubber. This is because in the example illustrated, the left positive model 7 is larger than the left positive model 11 to the extent of the thickness of the artificial mamma, and the shape of the inner surface of the plaster negative model 8 determines the shape and size of the resultant artificial mamma. However, the difference in size is generally very small and usually does not cause users to feel discomfort when using the artificial mamma and may even be minimized during production, for example, by shaving the plaster surface to the extent of the thickness of the silicon rubber to obtain a sufficiently desirable artificial mamma.

It will be appreciated that application of the model according to the present invention should not be limited to the case where the left or right mamma is provided in a reverse feature to the other. The invention when applied to any other case does naturally not require the model-reversing process.

FIG. 11 is a partially cut-out perspective view showing an example of an artificial mamma according to the present invention obtained above. As clearly shown in FIG. 11, the artificial mamma 20 according to the present invention comprises a skin 21 including an elastic fabric layer 15 and a silicon rubber layer 12 enclosing the elastic fabric layer 15. The inner space 22 is cut off from the outside and given suitable elasticity by air. As a result, the outside part of the skin 21 shaping the real mamma when touched or depressed feels substantially similar to that of the real mamma.

A nipple part 23 which is shaped like a real nipple has inside a lump-like shaped larger thickness portion serving as a simple valve for injecting and exhausting air. The specific structure of the simple valve depends on the shape and structure of the air injection needle to be used. When the air injection needle employs a sharp-edged needle, such as an injector needle, provision of only the lump-like larger thickness portion can constitute the valve. The feature is similar to an air-injecting portion of a child's rubber ball.

The skin 21 comprises a surface part with an outward appearance shaping a real mamma and a rear side part joined with the surface part and adapted to be contacted directly with the user's skin. It will be appreciated that the surface part is made by use of the foregoing negative model 1. The rear side part similarly comprises a main body made of silicon rubber and elastic fabric layer 15. The silicon rubber is compatible with human skin and there is thus a reduced possibility of the occurrence of skin eruptions or enanthema which may result when other materials are used. However, these effects may be further reduced by spreading or coating an antiperspirant agent, such as baby powder or the like, on the rear side part of skin 21.

As explained above, the artificial mamma according to one embodiment of the present invention has the following advantages:

1) The artificial mamma is covered with silicon rubber to reduce the possibility of the occurrence of excessive inflammation of the human skin in contact with the artificial mamma.

2) The artificial mamma is in the form of an air bag and is lighter than conventional devices, so that it is not uncomfortable in use and does not require any additional undergarments.

3) The artificial mamma has a larger thickness part through which air is injected and exhausted by use of an air injection needle, so that fine adjustment of the elasticity of the artificial mamma can be simply carried out.

Also, the negative model for the artificial mamma according to a further embodiment of the present invention has the following advantages:

1) The negative model can be easily made at home without a special workshop or facilities, merely by applying aluminum foil to a real mamma serving as an original model (a left or right real mamma opposite to an intended artificial mamma will suffice) and covering the outer surface of the aluminum foil with the foamable-hardening type plastic material.

(2) Cost to produce the negative model is low.

(3) The negative model has enough strength that it may be mailed and will retain its shape. Also, the negative model comprises a thin aluminum foil and plastic foam which is quite light, readily handled and low in mailing cost.

It should be apparent to those skilled in the art that various modifications may be made to the disclosed embodiments without departing from the spirit or scope of the invention, as limited only by the claims.

We claim:

1. A method of making a negative model for an artificial breast comprising the following steps:

applying aluminum foil to a breast;

deforming the aluminum foil to correspond to the breast; and coating the aluminum foil with a foam-hardening type of urethane resin liquid, wherein the negative model to produce the artificial breast is formed according to a first breast which is opposite a second breast location where the artificial breast is to be placed, the negative model having a first side for producing an artificial breast corresponding to said first breast and a second side for producing an artificial breast corresponding to said second breast location, the first side and the second side being reversed with respect to each other.

2. A method of making a positive model for an artificial breast and a negative model comprising the following steps:

applying plaster to an aluminum model to form a first positive model;

removing the aluminum model;

coating the first positive model with aluminum foil;

reinforcing the aluminum foil with adhesive taping;

removing the aluminum foil and adhesive taping from the first positive model;

reversing the aluminum foil and adhesive taping by applying pressure on the adhesive taping to form a reversed aluminum foil model;

applying plaster to the reversed aluminum foil model to form a second positive model having an outer surface;

removing the reversed aluminum foil model;

treating the outer surface of the second positive model; and applying plaster to the positive model to form a negative model, said negative model having an inner surface said first positive model corresponding to one of a left and right breast of a person, and said second model corresponding to the other of said left and right breast of a person.

3. The method of making a positive model and a negative model according to claim 2 further comprising the steps of:

applying foamable plastic to the inner surface of the negative model to form an inner plastic surface having a thickness substantially equivalent to the artificial breast; and applying plaster to the inner plastic surface to form a final positive model.

4. A method of making a positive model, a negative model and an artificial breast comprising the following steps:

applying plaster to an aluminum model to form a first positive model;

removing the aluminum model;

coating the first positive model with aluminum foil;

reinforcing the aluminum foil with adhesive taping;

removing the aluminum foil and adhesive taping from the first positive model;

reversing the aluminum foil and adhesive taping by applying pressure on the adhesive taping to form a reversed aluminum foil model;

applying plaster to the reversed aluminum foil model to form a second positive model having an outer surface;

removing the reversed aluminum foil model;

treating the outer surface of the second positive model;

applying plaster to the positive model to form a negative model; and injecting silicon rubber melt between the positive model and the negative model to form the artificial breast, said first positive model corresponding to one of a left and right breast of a person, and said second model corresponding to the other of said left and right breast of a person.

5. The method of making a positive model, a negative model and an artificial breast according to claim 4 wherein elastic fiber is injected between the positive model and the negative model.

6. The method of making a positive model, a negative model and an artificial breast according to claim 4 wherein the second positive model is shaved by a thickness substantially equivalent to the artificial breast.

7. A method of making a positive model, a negative model and an artificial breast comprising the following steps:

applying plaster to an aluminum model to form a first positive model;

removing the aluminum model;

coating the first positive model with aluminum foil;

reinforcing the aluminum foil with adhesive taping;

removing the aluminum foil and adhesive taping from the first positive model;

reversing the aluminum foil and adhesive taping by applying pressure on the adhesive taping to form a reversed aluminum foil model;

applying plaster to the reversed aluminum foil model to form a second positive model having an outer surface;

removing the reversed aluminum foil model;

treating the outer surface of the second positive model;

applying plaster to the positive model to form a negative model; said negative model having an inner surface applying foamable plastic to the inner surface of the negative model to form an inner plastic layer having a thickness substantially equivalent to the artificial breast;

applying plaster to the inner plastic layer to form a final positive model;

removing the inner plastic layer; and injecting silicon rubber melt between the final positive model and the negative model to form the artificial breast, said first positive model corresponding to one of a left and right breast of a person, and said second model corresponding to the other of said left and right breast of a person.

8. The method of making a positive model, a negative model and an artificial breast according to claim 7 wherein the inner plastic layer is treated with a release agent.

9. The method of making a positive model, a negative model and an artificial breast according to claim 7 wherein elastic fiber is injected between the final positive model and the negative model.

10. The method of making a positive model, a negative model and an artificial breast according to claim 7 wherein the foamable plastic is applied such that it has a lump-like shaped larger thickness part at a point corresponding to a nipple.

* * * * *